US 11,399,983 B2

(12) United States Patent
Leeds

(10) Patent No.: US 11,399,983 B2
(45) Date of Patent: Aug. 2, 2022

(54) NEGATIVE PRESSURE THERAPY UNIT AND METHOD

(71) Applicant: Steel Trap Enterprises, LLC, Las Vegas, NV (US)

(72) Inventor: Steven Leeds, Dallas, TX (US)

(*) Notice: Subject to any disclaimer, the term of this patent is extended or adjusted under 35 U.S.C. 154(b) by 0 days.

(21) Appl. No.: 16/648,881

(22) PCT Filed: Sep. 19, 2017

(86) PCT No.: PCT/US2017/052308
§ 371 (c)(1),
(2) Date: Mar. 19, 2020

(87) PCT Pub. No.: WO2019/059893
PCT Pub. Date: Mar. 28, 2019

(65) Prior Publication Data
US 2020/0276056 A1    Sep. 3, 2020

(51) Int. Cl.
*A61F 13/00* (2006.01)
*A61M 1/00* (2006.01)

(52) U.S. Cl.
CPC ......... *A61F 13/00068* (2013.01); *A61M 1/90* (2021.05); *A61F 2013/00357* (2013.01); *A61M 2205/32* (2013.01)

(58) Field of Classification Search
CPC .... A61F 13/00068; A61F 2013/00357; A61M 1/90; A61M 2205/32; A61M 1/87; A61M 1/916; A61M 1/84
See application file for complete search history.

(56) References Cited

U.S. PATENT DOCUMENTS

| | | | | |
|---|---|---|---|---|
| 2004/0093026 | A1* | 5/2004 | Weidenhagen | A61M 27/00 606/215 |
| 2005/0065484 | A1* | 3/2005 | Watson | A61M 27/00 604/289 |
| 2013/0165821 | A1* | 6/2013 | Freedman | A61F 13/0279 601/2 |
| 2014/0005479 | A1* | 1/2014 | Loske | A61B 1/273 600/115 |
| 2014/0088622 | A1* | 3/2014 | Rousseau | A61F 2/04 606/153 |

OTHER PUBLICATIONS

Definition of Radiopaque; https://www.merriam-webster.com/dictionary/radiopaque (Year: 2021).*

* cited by examiner

*Primary Examiner* — Philip R Wiest
*Assistant Examiner* — Gregory J Feulner
(74) *Attorney, Agent, or Firm* — Law Office of Jeff Williams PLLC; J. Oliver Williams

(57) ABSTRACT

A negative pressure therapy unit is disclosed that is designed for healing internal wounds under the application of negative pressure. A plurality of tubes sequentially movable relative to one another are used to locate a filler material inside the organ. The tubes cover the filler material to avoid contact with the organ and filler material. A pressure tube passes internally to the plurality of tubes and communicates with the filler material. The filler material is in a compressed state between at least one of the plurality of tubes and the pressure tube. Translation of one of the plurality of tubes selectively exposes the filler material and permits the filler material to expand into the wound. The filler material is interchangeable on the wound and selectively on the pressure tube.

18 Claims, 8 Drawing Sheets

NEGATIVE PRESSURE THERAPY UNIT AND METHOD

TECHNICAL FIELD

The present invention relates to a medical device and method and more particularly to a negative pressure therapy unit with a selectively deployable sponge to help close and heal open wounds inside the human body.

DESCRIPTION OF THE PRIOR ART

Presently, negative pressure wound therapy devices and processes are used in the medical profession. These are used to clean wounds, reduce bacterial counts through debridement, promote granulation and epithelialization for stimulating cell growth. Traditionally this involves placing a vacuum dressing over the wound. The general process includes placing a skin barrier on the skin, locating a filler material in the wound, and followed by placing a transparent film over the filler material. A vacuum tube is in communication with the filler material. Vacuum or negative pressure is generated within the sealed filler material which acts to draw the wound to the filler material. Filler material may be foam dressings, cotton gauze, and even non-woven polyester. The filler material can be selected based partly on the type of wound being treated. This process has typically been used with external wounds to the body and is useful in trying to avoid the need to involve intrusive surgical procedures.

Some attempts have been made to use this same vacuum/negative pressure therapy procedure internally as well. However, this has seen many complications. One of the main complications is that it becomes too difficult to get the sponge inside the body as it is exposed. Some attempts have been made with this approach in the colon area of the body but have been limited to wounds close to the rectum as a result of having to push the exposed filler material into the body. As attempted by some, a sponge is located on the end of a vacuum line and secured in various ways. The sponge is then pushed into the body or pulled with a tool. The nature of the sponge prevents this from progressing far. The sponge acts as a filler material. The sponge is located via a scope as best as can be detected through the lens. Once located, a negative pressure is created which causes the surrounding tissue and organs to collapse into the sponge.

As noted previously, a disadvantage of existing attempts to use negative pressure therapy internally is the limited reach inside the human body. An advantage of negative pressure therapy procedures is avoidance of surgical procedures. Therefore unless a method of locating a sponge within the body can be found, negative pressure therapy internally used will be vastly limited.

A new negative pressure therapy unit is needed to permit the useful benefits of negative pressure therapy to be had for internal wounds. Although great strides have been made, considerable shortcomings remain.

SUMMARY OF THE INVENTION

The present application discloses a unit that is configured to permit negative pressure therapy treatments internally to a body. The system is configured to include a plurality of tubes selectively overlapping one another to cleanly and accurately locate a filler material in position relative to an internal wound. The filler material is able to be sized according to the wound. Additionally the filler material is configured to be routed in a compressed and protected condition to allow for a streamlined package and to avoid direct resistance from the body in contact with the filler material. The compact nature of the unit of the present application will permit its use in any location accessible to medical professionals through any exterior orifice of the body.

The process includes locating the unit with any number of tools, such as a scope or even through X-ray using radio-opaque markers. Once located, the filler material is exposed and expanded into the wound area. A vacuum pressure is applied equally throughout the filler material to draw in the wound so as to close around the filler material. The vacuum pressure is passed through a tube having one or more apertures distributed along the length of the filler material. Periodically, the filler material is adjusted and may be loosened from the wound to prevent a permanent closure on the filler material. A sponge is a suitable filler material and it compresses well, holds shape, and accepts the vacuum pressure.

The more important features of the system have thus been outlined in order that the more detailed description that follows may be better understood and to ensure that the present contribution to the art is appreciated. Additional features of the system will be described hereinafter and will form the subject matter of the claims that follow.

Many objects of the present system will appear from the following description and appended claims, reference being made to the accompanying drawings forming a part of this specification wherein like reference characters designate corresponding parts in the several views. For example, it is an object of the present application to provide a device or unit that permits for the internal transportation of a filler material inside a body. The filler material is designed to be selectively exposed. It is also an object of the present application to provide a unit that can be monitored or located through a plurality of ways, apart from just the scope.

Before explaining at least one embodiment of the system in detail, it is to be understood that the system is not limited in its application to the details of construction and the arrangements of the components set forth in the following description or illustrated in the drawings. The system is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the various purposes of the present system. It is important, therefore, that the claims be regarded as including such equivalent constructions insofar as they do not depart from the spirit and scope of the present system.

BRIEF DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

Figure 1:
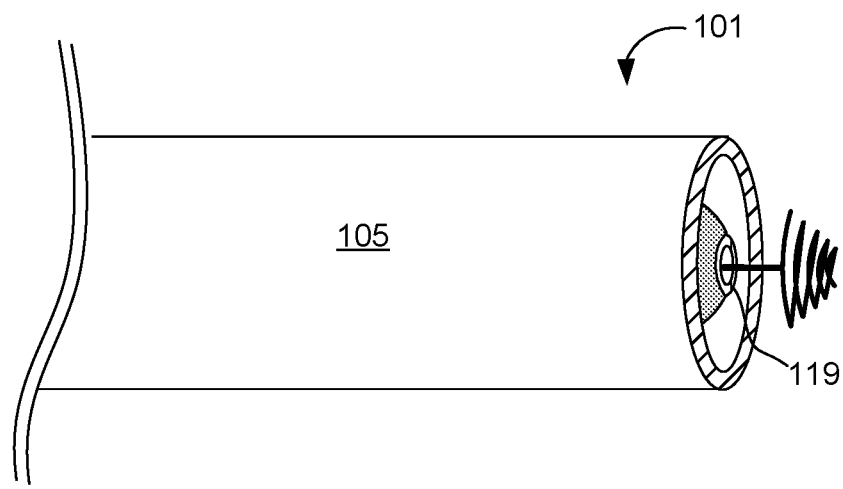
FIG. 1 is a partial perspective view of the negative pressure therapy unit according to an embodiment of the present application.

While the unit and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The system in accordance with the present application overcomes one or more of the above-discussed problems commonly associated with existing methods and devices of healing wounds through negative pressure therapy. Specifically, the unit and method of the present application includes a selectively deployable filler material that is initially guarded from contact with the human body. The filler material is selectively exposed and uncovered from within the unit when located adjacent the wound to be healed. The unit of the present application may use many techniques to operate or locate the device including X-ray and scopes. The negative therapy unit of the present application is routable to any internal location within the body. Some embodiment of the present invention are able to selectively restrict closure of the particular organ around the filler material by restricting the size and shape of the filler material. This permits the continued body functions of the organ and helps minimize difficulties to the patient. These and other unique features of the system are discussed below and illustrated in the accompanying drawings.

The unit will be understood, both as to its structure and operation, from the accompanying drawings, taken in conjunction with the accompanying description. Several embodiments of the assembly are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

The unit of the present application includes a plurality of tubes sequentially movable relative to one another. The tubes include an outer sheath and an inner sheath. The outer sheath overlaps the inner sheath. A pressure tube is located through the plurality of tubes for the application of pressure to a filler material. The unit includes a filler material compressed between an outer sheath and the pressure tube. It is understood that no vacuum pressure is applied to the tube to maintain the compressed state of the filler material. A plurality of ports exist in the pressure tube adjacent an interior surface of the filler material. Translation of the outer sheath away from the distal end of the unit exposes the filler material to the internal wound. When exposed, the filler material expands. A negative pressure therapy is then applied through the pressure tube. Detecting the location of the filler material in the human body can be done through use of a radio-opaque material in communication with any of the tubes, or through the use of a scope. These and other unique features of the system and method are described herein below.

Referring now to the figures wherein like reference characters identify corresponding or similar elements in form and function throughout the several views. The following Figures describe system 99 and its associated features. With reference now to the drawings, an embodiment of the automatic car air freshener system are herein described. It should be noted that the articles "a", "an", and "the", as used in this specification, include plural referents unless the content clearly dictates otherwise.

Referring now to FIG. 1 in the drawings, a partial perspective view of a negative pressure therapy unit 101 according to an embodiment of the present application is illustrated. Unit 101 is configured to introduce a filler material into a human body through a natural orifice, such as the mouth and rectum, for the application of negative pressure therapy to an internal wound of the body. System 101 is configured to selectively cover or hide the filler material from contact with the inner portions of the body. Doing so makes it possible to reach internal areas away from an entrance point of the body. As filler material tends to be dry and rough textured due to its porous nature, leaving it exposed inside the body restricts its ability to travel internally. Unit 101 uncovers or exposes the filler material when it is located adjacent the wound so as to make translation into the body relatively simple.

Figure 2:
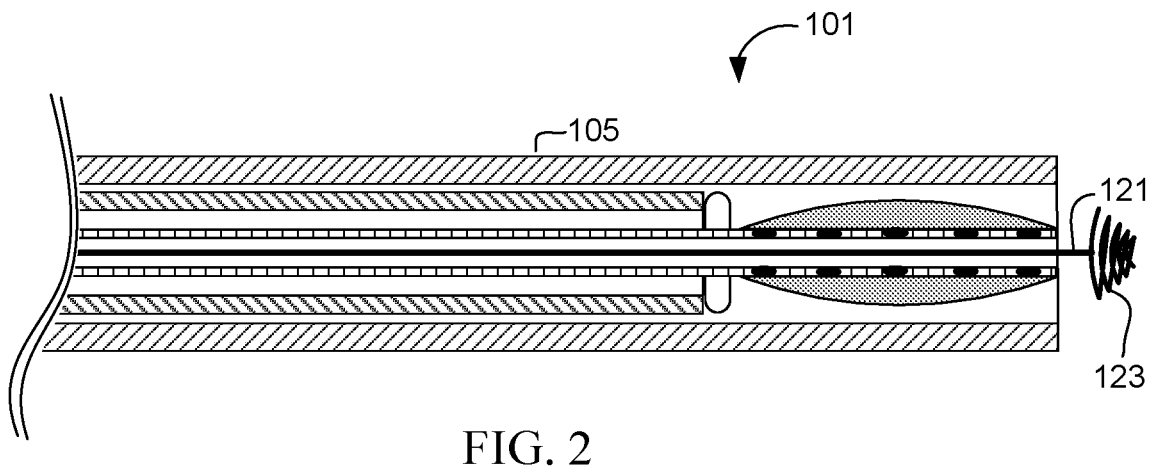
FIG. 2 is a section view of the negative pressure therapy unit of FIG. 1.
Figure 3:
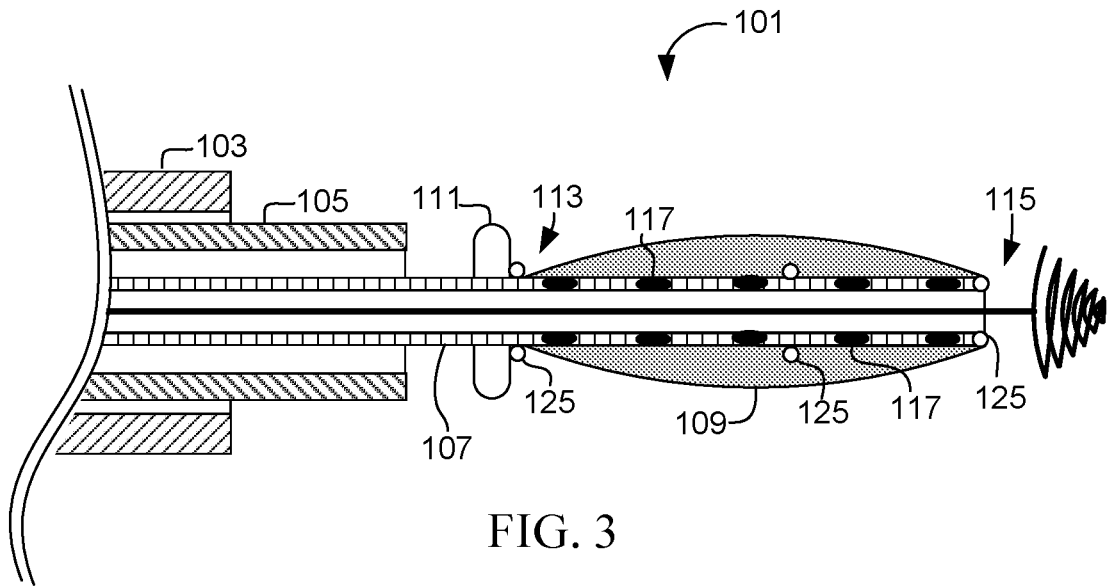
FIG. 3 is an alternative section view of the negative pressure therapy unit of FIG. 2 having a series of components moved in relation to one another for clarity.

Referring now also to FIGS. 2 and 3 in the drawings, side section views of unit 101 are illustrated. FIG. 2 illustrates a side view of the unit as seen in FIG. 1. FIG. 3, on the other hand, attempts to more clearly illustrate the various components of unit 101 by showing the plurality of tubes translated relative to one another. Unit 101 includes a plurality of tubes used to transport a filler material 109 inside a human body. The tubes include an outer sheath 103 and an inner sheath 105. Within inner sheath 105 is a pressure tube 107 used to supply a negative pressure to filler material 109. Outer sheath is configured to translate over inner sheath 105 and filler material 109.

Sheaths 103 and 105 can be made from typical medical grade tubing. A seal is not required between them. They are configured to allow minimal friction between themselves to permit free translation. Inner sheath 105 is configured to assist in maintaining the location of filler material 109 once located and as outer sheath 103 is removed.

Unit 101 further includes a bumper 111. Bumper 111 is coupled to pressure tube 107 adjacent filler material 109. Bumper is on a proximal end 113 of filler material 109. Bumper 111 acts as a stop for inner sheath 105 during operation. As sheath 103 is removed, inner sheath 105 counteracts the outward motion and force of sheath 103 by generally contacting bumper 111. Bumper 111 is shown as being a ringed component wrapped around the circumference of pressure tube 107, however, it is understood that bumper 111 is not limited to such a configuration. For example, bumper 111 may consist of a plurality of knobs, bumps, or tabs extending out from pressure tube 107.

Pressure tube 107 extends through inner sheath 105 and within filler material 109. Ideally pressure tube 107 ends at a distal end 115 of filler material 109 but may extend a distance further. As seen from FIG. 1, in transportation through the internal areas of the body, outer sheath 103 fully covers filler material 109 and pressure tube 107. At distal end 115, pressure tube 107 ends such that the tube is uncapped at tip 119 permitting the passage of air to pass through its end. Further included in pressure tube 107 are a plurality of ports 117 adjacent filler material 109. Ports 117 are configured to pass through tube 107 and are distributed along the length of tube 107 in the region of filler material 109. Given the porous nature of filler material 109, air drawn through tube 107 will be pulled through tip 119 and ports 117.

As seen best in FIG. 2, filler material 109 is shown in a compressed state when covered by outer sheath 103. The compressed state is necessary to aid in translating unit 101 through the human body. By maintaining a minimal diameter, less resistance and fewer obstructions are realized. Filler material 109 is configured to assist in the growth and healing of human tissue when applied in direct contact with the tissue and subjected to a negative pressure to maintain such contact. Therefore, to help drawn in the human tissue around material 109, material 109 must have a porous characteristic to allow air to pass there through. Under negative pressure, air in the body is drawn through material 109 and pulls the tissue into contact.

Filler material 109 may be made from many different products. Ideally it is conceived that a good type of material is that of a sponge. The material is to be porous and compressible. A sponge allows for a great level of expansion and compression. Additionally, the material composition of filler material 109 is configured to have a memory to maintain its natural relax state after being compressed for a given duration. Filler material 109 may be coupled to tube 107 for a given time in a compressed state. In another embodiment, unit 101 may be preassembled but outer sheath 103 is withdrawn from material 109 such that material 109 is stored in a relaxed state prior to use. Alternatively, some configurations of unit 101 may allow for filler material to be customized in size and shape and attached (i.e. via an adhesive or fastener) to tube 107 at the time of use (not fully preassembled). In this manner material 109 may be detachable and fully customizable. Whether permanently bonded in a preformed package or customized and compressed at time of use, the compressibility of material 109 is important.

It is understood that material 109 may be biodegradable, non-degradable, made from a biologic material, and absorbable. It is also understood that depending on the material selection, compressing of filler material 109 may act to alter its length. Furthermore is should be known that although the description of unit 101 is made in relation to a human body, it is not limited thereto. For example, unit 101 and its associated process may work equally well with that of animal bodies.

Also seen in FIGS. 2 and 3 are other components for use with unit 101. For example, unit 101 may further include a guide wire 121. Wire 121 is configured to be run within pressure tube 107. A use of wire 121 is that during installation, wire 121 may be located first with a scope and then unit 101 may be run along its length until unit 121 is in position. The correct position is determined by contact with a coil tip 123 of wire 121. Tip 123 is sized so as to at least contact tube 109 or outer sheath 103.

Additionally, unit 101 may further include a radio-opaque material 125 to help define the location of material 109 inside the body. This is useful if a scope is not used as some medical professionals prefer a method using X-ray. Material 125 is visible under X-ray. Material 125 may be included within the material make-up of any one of sheaths 103, 105, tube 107, material 109, and bumper 111. Radio-opaque material 125 is selectively located in unit 101 to define the location of filler material 109. This is done partly by locating material 125 at proximal 113 and distal ends 115 of filler material 109 along with a centrally located position within filler material 109. As seen in FIG. 3, material 125 is a separate material in communication with that of tube 107. By incorporating it into bumper 111 and/or tube 107, a medical professional may consistently assess the location of material 109 event after sheaths 103 and 105 are withdrawn.

Referring now also to FIGS. 4-11 in the drawings, a sequential series of figures are shown to illustrate the method of using unit 101 within the body. Unit 101 will be depicted in use with a scope 127. Unit 101, wire 121, and scope 127 are shown in the assorted views within an organ 129 of a body 131. It is understood that a similar process will be realized from reliance upon radio-opaque material 125.

Figure 4:
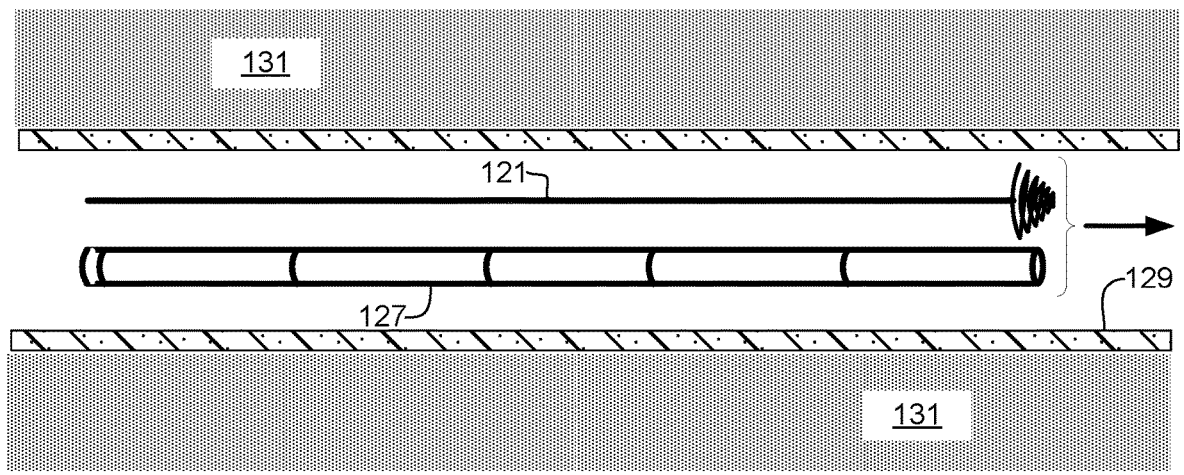
FIGS. 4-11 are exemplary side section views of the negative pressure therapy unit of FIG. 1 shown in use to close a wound.
Figure 5:
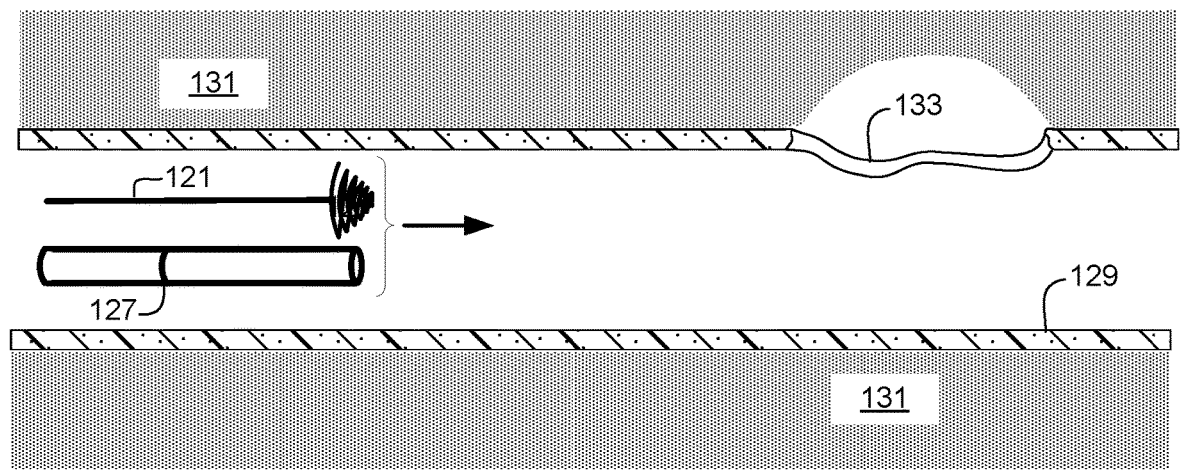
Figure 6:
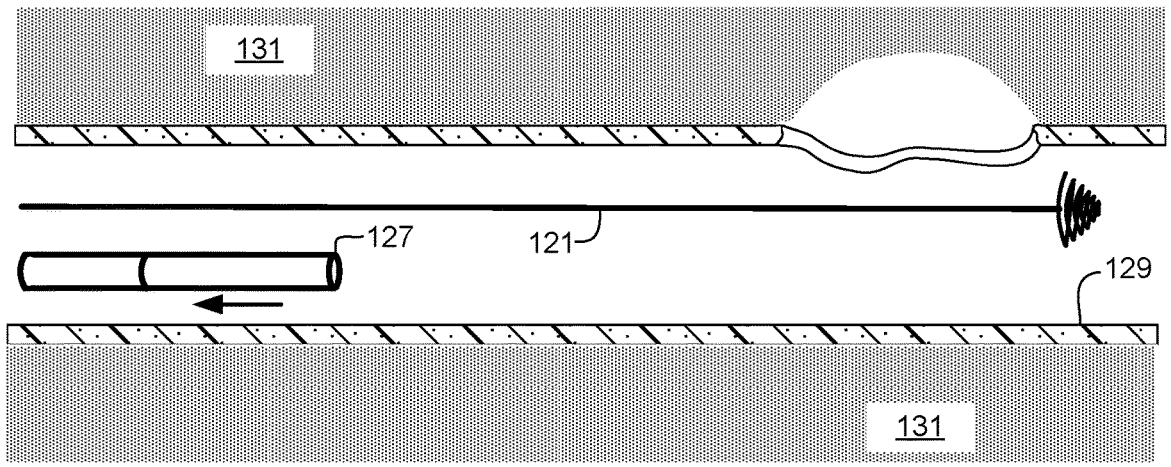

From the figures it is shown that scope 127 and wire 121 are passed through organ 129 until they reach wound 133 (FIGS. 4 and 5). Wound 133 is an internal would in the body and can be in any known organ, such as the colon, gastro-intestinal tract (i.e. stomach and intestines), esophagus, or other place. As stated previously, unit 101 is passed through an existing orifice of the body. In some situations the orifice may be a cut section of skin. Upon reaching wound 133, scope 127 is removed while wire 121 remains in position. Coil tip 123 is located on a far edge of wound 133 (FIG. 6).

Figure 7:
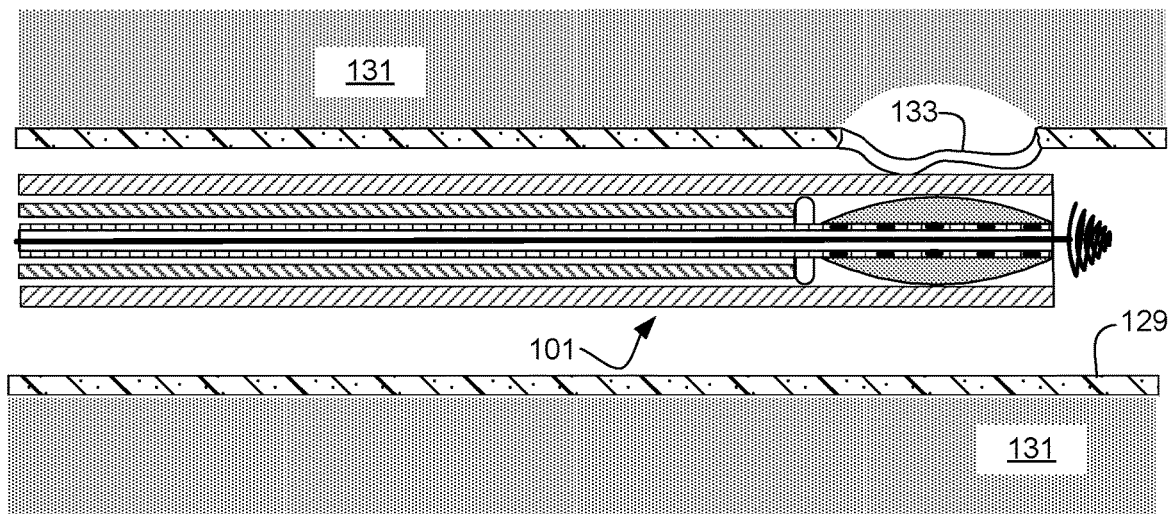
Figure 8:
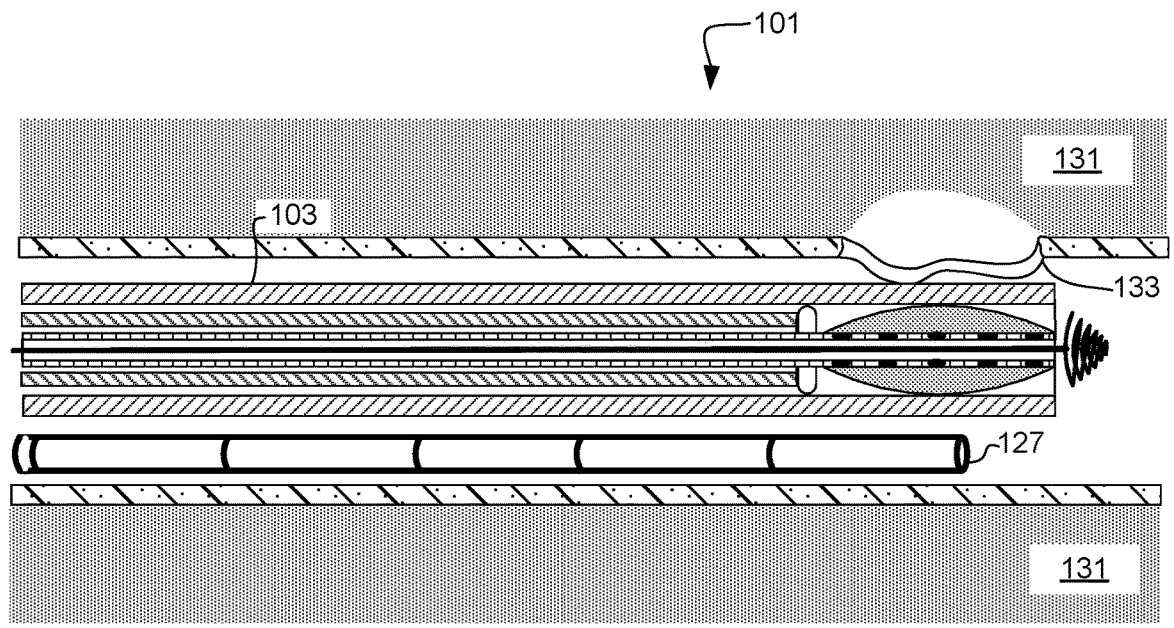
Figure 9:
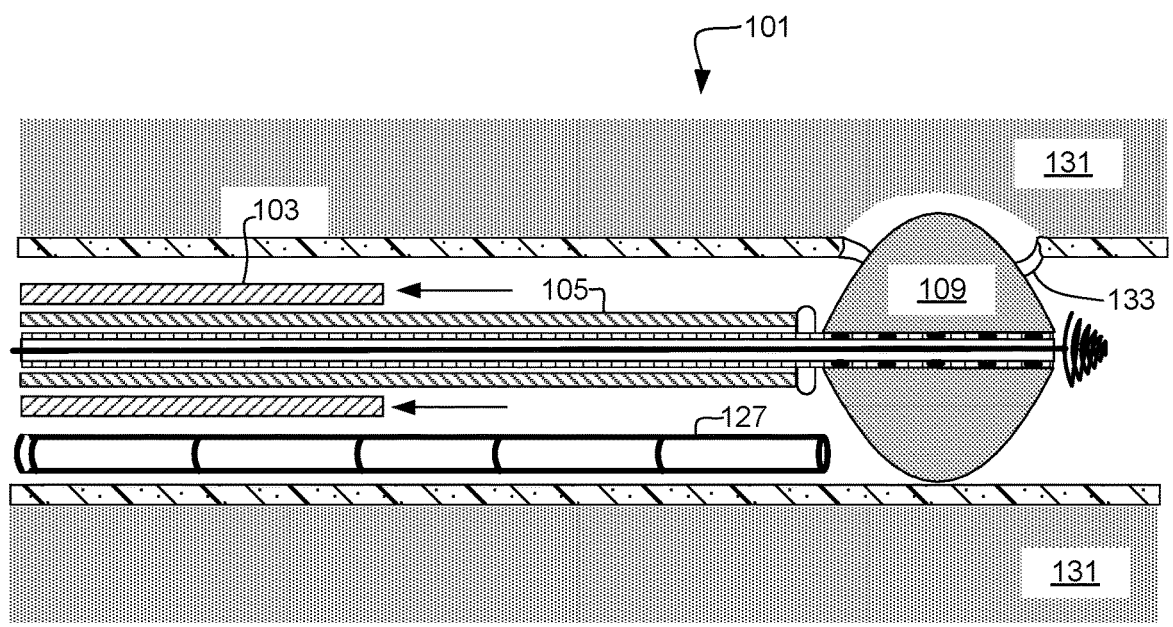
Figure 10:
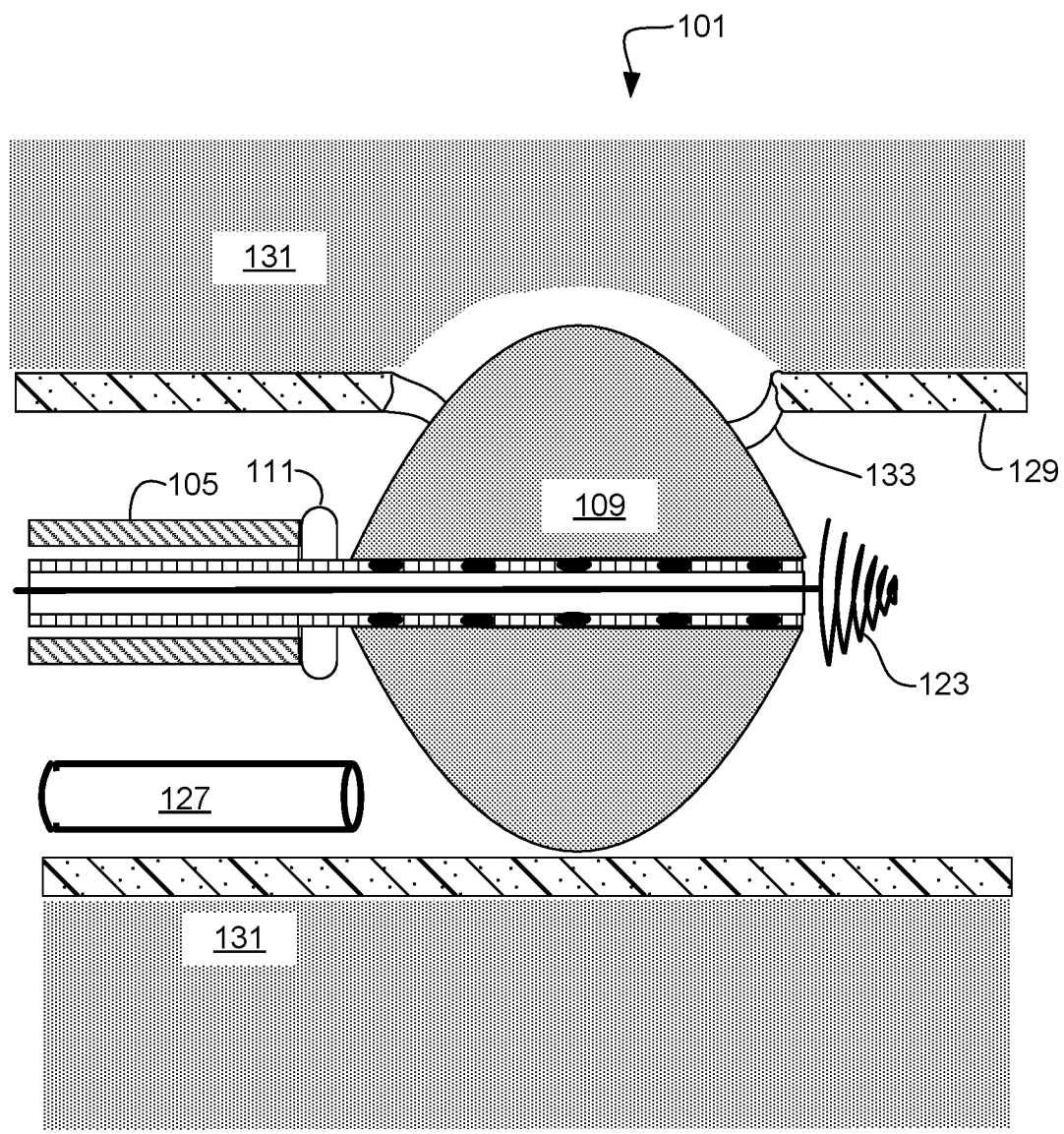

Unit 101 is then passed along wire 121 and within organ 129 until it contacts tip 123. It is understood that a loop may be formed around the tip of unit 101 to aid in pulling unit 101 into position relative to tip 123. The loop can be clasped by scope 127 and pulled to aid in passing within organ 129. The loop may pass through at least one of filler material 109 and tube 107. Once unit 101 reaches tip 123, a medical professional knows that unit 101 is in position relative to wound 133 (FIG. 7). Scope 127 is passed back through organ 129 to permit the medical professional to view the performance of unit 101 (FIG. 8). This assumes that scope 127 was not already used to located unit 101 with the loop. Once unit 101 is in position, outer sheath 103 is removed from unit 101 sufficiently to permit filler material 109 to expand into an uncompressed state (FIG. 9). When uncompressed, material 109 expands into wound 133. During removal of sheath 103, inner sheath 105 is used to maintain the proper location of material 109 by contacting bumper 111 so as to prevent tube 107 from withdrawing simultaneously. FIG. 10 illustrates an enlarged view of filler material in an uncovered and expanded state.

Figure 11:
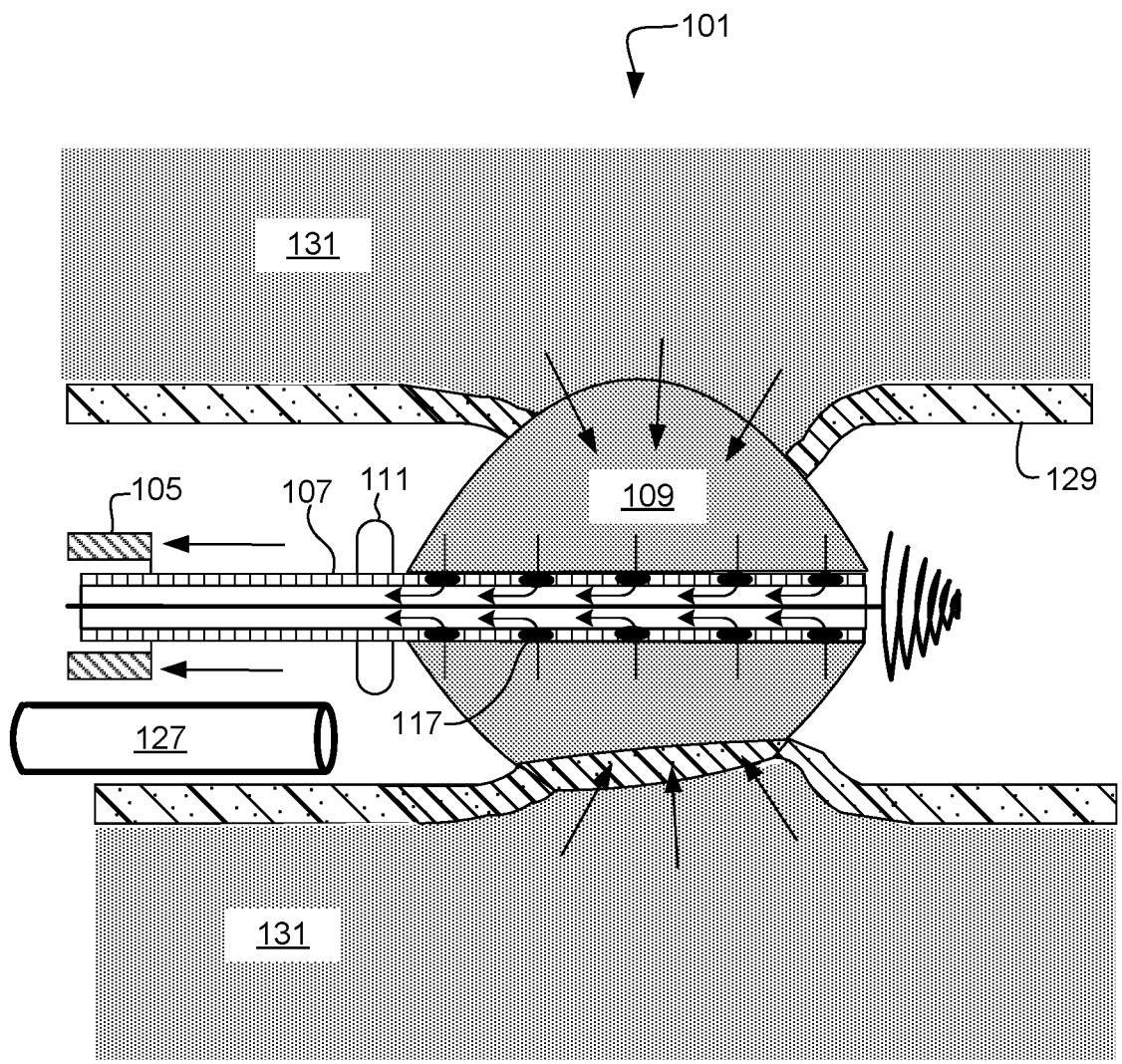

Once expanded, a negative pressure is introduced into pressure tube 107 which acts with suck in the air within organ 129. This suction draws with organ 129 and body 131 to filler material 109. Arrows in FIG. 11 are used to illustrate the flow direction of air within organ 129. Air is seen passing through material 109 and extending through ports 117. Although an arrow is not shown at tip 119, it is understood that air is passing there through as well. The level of negative pressure is maintained to some degree for the duration of treatment. It is also worth noting that inner sheath 105 is removed once negative pressure has been applied and filler material is secured to organ 129 and wound 133.

Figure 12:
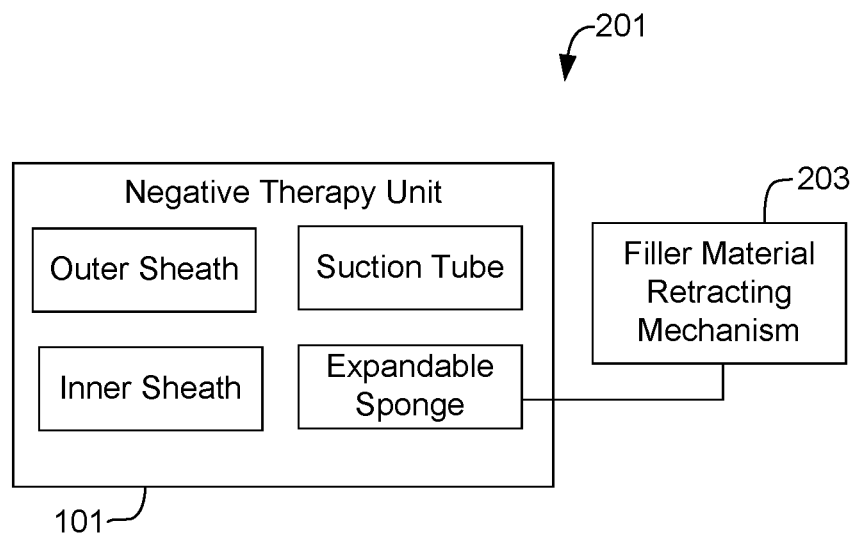
FIG. 12 is a chart of an alternative embodiment of the negative pressure therapy unit of FIG. 1.

Referring now also to FIG. 12 in the drawings, a chart of an alternative embodiment of unit 101 is illustrated. Unit 201 is similar in form and function to that of unit 101 except as noted herein. Unit 201 includes unit 101 and a retracting mechanism 203. Mechanism 203 is configured to communicate with filler material 109 to apply a force such that it at least partially recompresses filler material 109. This may be done where mechanism 203 includes hooks or teeth set within material 109 and that pull inwardly so as to recompress the filler material. Mechanism 203 is configured to separate filler material 109 from that of wound 133, organ 129, and body 131. Once separated, outer sheath 103 may selectively be reinserted over filler material 109 for removal from organ 129. The process of inserting and removing material 109 may be done a plurality of times over the course of a single set of treatments. Often filler material 109 has to be replaced after a number of days over the wound.

Figure 13A:
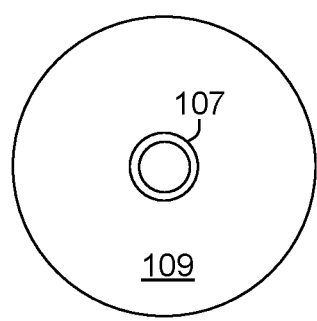
FIG. 13A-13C are end views of a filler material for use in the negative pressure therapy unit of FIG. 1.
Figure 13B:
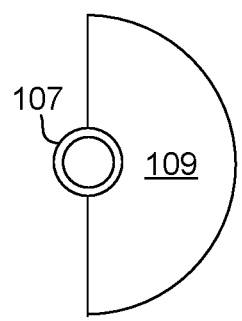
Figure 13C:
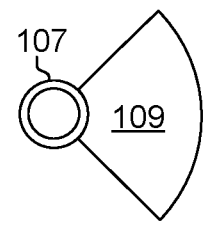

Referring now also to FIGS. 13A-13C in the drawings, end views of pressure tube 105 and filler material 109 are illustrated. These are exemplary embodiments showing various shapes to which material 109 may be formed. As seen in FIG. 13A, material 109 is formed around the entire circumference of tube 105. It is this embodiment of material 109 that is shown in the prior figures. Additionally, material 109 may be shown in either a half circular (FIG. 13B) or quarter circular shape (FIG. 13C).

Different shapes of filler material 109 can be important. As seen in FIG. 11, application of a vacuum pressure often will lead to a full enclosure of organ 129 in an effort to draw wound 133 to filler material 109. Fully closing organ 129 can lead to additional difficulties to a patient during recovering and healing. Depending on the location of wound 133, this may lead in an inability to eat normally through ones esophagus or digest food through an intestine. As healing from the wound 133 may take a number of weeks, the fully closing of organ 129 can result in patients having longer hospital stays, experiencing more expense, and increased discomfort. By adjusting the shape of filler material 109, the location of ports 117, and the proximity of unit 101 to the wound 133, a medical professional may be able to experience only a partial closure of organ 129.

It is conceive that some embodiments of units 101/201 may include clasps that affix unit 101 to organ 129 around the wound such that a general sealing effect would be realized. Therefor a controlled directional application of negative pressure to only the wound would allow the opposing walls of organ 129 to not experience the negative pressure. Organ 129 would then be free to operate during the healing process. In this embodiment, unit 101 creates a relative sealing effect around wound 133 prior to application of the negative pressure.

Figure 14:
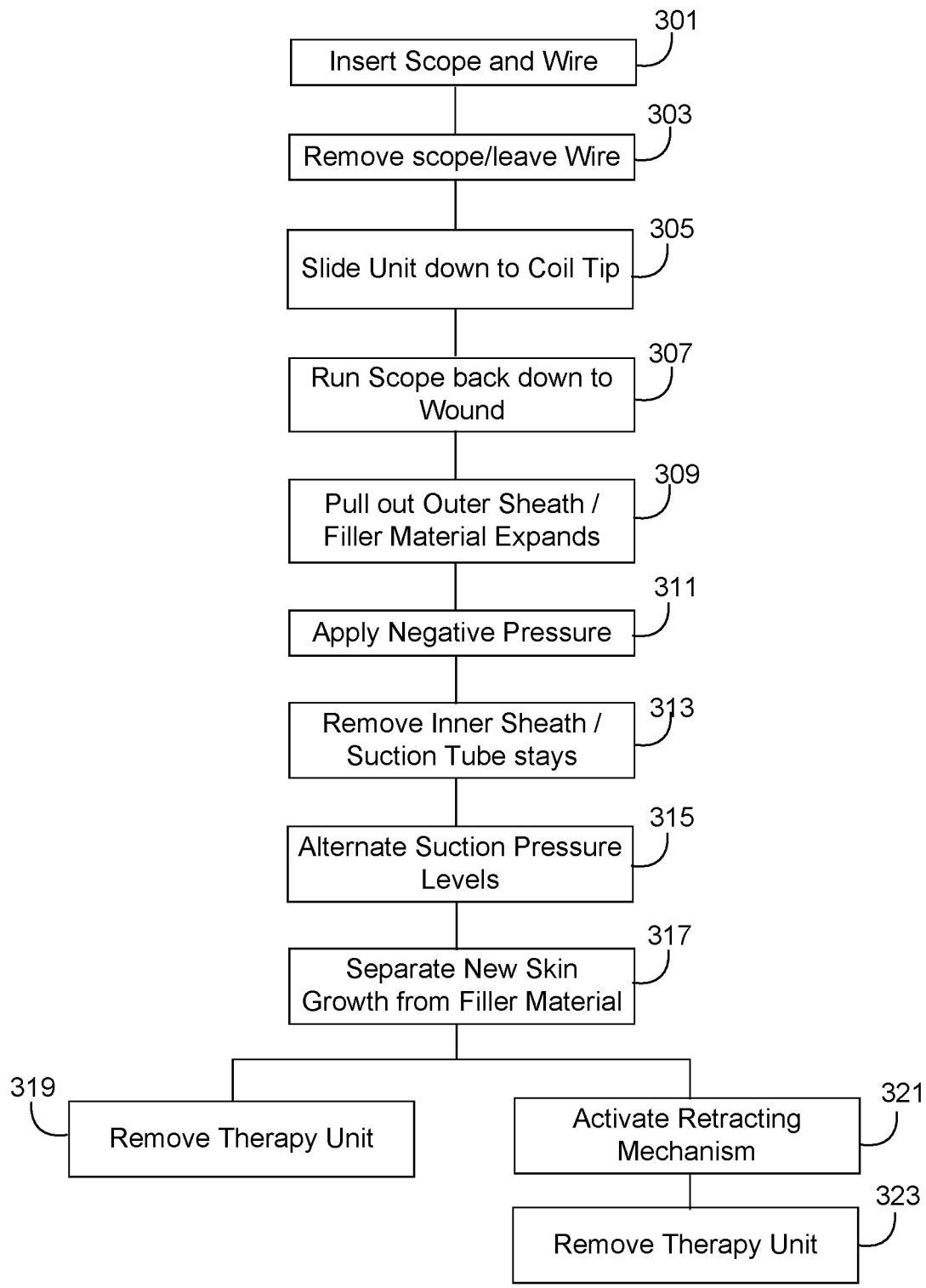
FIG. 14 is a chart of a method of use for the negative pressure therapy unit of FIG. 1.

Referring now also to FIG. 14 in the drawings, a chart of the method of using unit 101 is illustrated. Much of these steps have been described above but are herein reiterated to simplify the process and make it more clear. A scope and wire are inserted into the body within an organ (301) until they reach the wound area. The wire is positioned properly in relation to the wound. The scope is removed (303) and the wire is left in place to act as a method of positioning the unit of the present application. Unit 101 is slid down the wire until it contacts the coil tip (305). The scope is run back down the organ to provide visual frame of reference to the medical professional (307). The outer sheath is removed (309) to expand the filler material into the wound. A negative pressure is introduced through the pressure tube (311) to draw the wound into contact with the filler material. The negative pressure may either vary intermittently or remain at a constant level during treatment (315). The inner sheath is removed (313). Over time, treatment often requires the replacing of filler material similar to that of typical gauze on a wound. Periodically the filler material and organ are detached (317) for interchanging of the filler material. Filler material 109 may be detachable from pressure tube 107 as noted above. When this is the case, a user reuses the other portions of unit 101 and simply reattaches a new filler material. When healing is complete, unit 101 is removed (319). Alternatively, the retracting mechanism may be used to retract the filler material (321) prior to removing the unit (323).

It is understood that in some procedures it is acceptable for scope 121 to pass internally within either of sheaths 103, 105 or pressure tube 107.

The current application has many advantages over the prior art including at least the following: (1) ability to treat internal wounds with a negative pressure therapy procedure; (2) a covered filler material to avoid contact with internal organs during routing; (3) compact design where the filler material is routed in a compressed state; (4) selective uncovering of the filler material to permit expansion adjacent the wound; (5) ability to interchange the filler material in communication with the pressure tube; (6) ability to recompress the filler material; and (7) ability to partially seal along a wall of the organ to permit functioning of the organ during treatment (i.e. not close off the organ with the application of negative pressure).

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

The invention claimed is:

1. A negative pressure therapy unit for healing internal wounds, comprising:
   a plurality of tubes sequentially movable relative to one another, the plurality of tubes including:
      an outer sheath; and
      an inner sheath, the outer sheath configured to surround and translate independent of the inner sheath;
   a pressure tube passing internally to the plurality of tubes;
   a filler material in communication with the pressure tube, the filler material selectively covered by the outer sheath, the filler material being in a compressed state between the outer sheath and the pressure tube, the pressure tube extending internally within the filler material;
   a bumper coupled to the pressure tube at a proximal end of the filler material; and
   a plurality of ports in the pressure tube located internally within the filler material, such that the plurality of ports extend along the length of the filler material to create a uniform pressure;
   wherein translation of the plurality of tubes selectively exposes the filler material and permits the filler material to expand into the wound; and
   wherein the inner sheath contacts the bumper so as to hold a position of the filler material and pressure tube relative to the internal wounds.

2. The unit of claim 1, wherein the pressure tube is open at a distal end.

3. The unit of claim 1, wherein the filler material is an endo-sponge.

4. The unit of claim 1, wherein the filler material is made from a biologic material.

5. The unit of claim 1, wherein the plurality of tubes translates relative to one another independently.

6. The unit of claim 1, wherein translation of the plurality of tubes uncompresses the filler material.

7. The unit of claim 1, wherein the location of the filler material is defined by a radio-opaque material.

8. The unit of claim 7, wherein the radio-opaque material is located adjacent the ends of the filler material.

9. The unit of claim 7, wherein the radio-opaque material is in included into a bumper at the proximal end of the filler material.

10. The unit of claim 1, further comprising:
    a radio-opaque material in communication with the pressure tube so as to define the location of the filler material in through X-ray.

11. The unit of claim 1, further comprising:
    a retracting mechanism configured to detach the filler material from the wound.

12. A method of treating an internal wound using negative pressure therapy, comprising:
    obtaining a filler material for the internal wound, the filler material being compressed between an outer sheath and a pressure tube, the pressure tube extending the length of the filler material;
    passing the outer sheath and filler material in a body such that the filler material is adjacent the internal wound;
    removing the outer sheath to expose the filler material to the internal wound, the filler material configured to expand into an uncompressed state;
    maintaining the position of the filler material during withdrawal of the outer sheath by contacting an inner sheath against a bumper located adjacent the filler material; and
    applying a negative pressure through the pressure tube to draw the internal wound to the filler material, the pressure tube having a plurality of ports extending the length of the filler material to create a uniform pressure on the filler material;
    wherein covering the filler material with the outer sheath permits passage of the filler material through one or more internal organs.

13. The unit of claim 12, further comprising:
    tracking the location of the filler material in the body by X-ray using a radio-opaque material.

14. The unit of claim 13, wherein the radio-opaque material is in communication with the pressure tube.

15. The unit of claim 12, further comprising:
    trimming the filler material to a particular size dependent upon the wound.

16. The unit of claim 12, further comprising:
    selectively retracting the filler material by transitioning from an uncompressed state into a compressed state.

17. The unit of claim 12, further comprising:
    periodically detaching the filler material from the wound.

18. The unit of claim 12, further comprising:
    attaching the filler material to the pressure tube.

* * * * *